US011813363B1

(12) United States Patent
Brady et al.

(10) Patent No.: US 11,813,363 B1
(45) Date of Patent: Nov. 14, 2023

(54) CONCENTRATED NUTRITIONAL OR SUPPLEMENTAL COMPOUND FOR INTESTINAL, GUT-BRAIN AXIS AND NEUROBIOLOGICAL HOMEOSTASIS THROUGH CALIBRATED ABSORPTION INCLUDING NEUROTRANSMITTER OR ANY EQUILIBRATING COMPOUND RELEASE TO TREAT OR MITIGATE DISEASE AND CO-MORBIDITIES, PARTICULARLY OBESITY AND MALNOURISHMENT

(71) Applicants: Terry Earl Brady, The Valley (AI); Anthony Lee Dellinger, Burlington, NC (US); Melinda K. M. Goddard, The Valley (AI); Lowell Hughes, The Valley (AI); Dick Luttekes, Philipsburg (SX)

(72) Inventors: Terry Earl Brady, The Valley (AI); Anthony Lee Dellinger, Burlington, NC (US); Melinda K. M. Goddard, The Valley (AI); Lowell Hughes, The Valley (AI); Dick Luttekes, Philipsburg (SX)

( * ) Notice: Subject to any disclaimer, the term of this patent is extended or adjusted under 35 U.S.C. 154(b) by 0 days.

(21) Appl. No.: 18/118,919

(22) Filed: Mar. 8, 2023

Related U.S. Application Data

(63) Continuation-in-part of application No. 17/952,691, filed on Sep. 26, 2022, now Pat. No. 11,771,125.

(51) Int. Cl.
| | | |
|---|---|---|
| *A61K 9/20* | (2006.01) | |
| *A61K 9/48* | (2006.01) | |
| *A61K 47/14* | (2017.01) | |
| *A23L 33/00* | (2016.01) | |

(52) U.S. Cl.
CPC ............ *A61K 9/4833* (2013.01); *A23L 33/40* (2016.08); *A61K 9/4825* (2013.01); *A61K 47/14* (2013.01)

(58) Field of Classification Search
CPC . A61K 9/14; A61K 9/141; A61K 9/16; A61K 9/1611; A61K 9/1605; A61K 9/19; A61K 9/20; A61K 9/2004; A61K 9/2022
See application file for complete search history.

(56) References Cited

U.S. PATENT DOCUMENTS

| | | |
|---|---|---|
| 5,063,073 A | 11/1991 | Kratochvil |
| 5,336,486 A | 8/1994 | Acharya |
| 5,654,028 A | 8/1997 | Christensen |
| 6,103,269 A | 8/2000 | Wunderlich |
| 6,426,077 B1 | 7/2002 | Grace |
| 8,562,952 B2 | 10/2013 | Lin |
| 2018/0289043 A1 | 10/2018 | Sannino |

FOREIGN PATENT DOCUMENTS

| | | | | |
|---|---|---|---|---|
| EP | 1247456 A2 | * | 10/2002 | ............ A23K 20/10 |
| MY | 186188 A | * | 6/2021 | ............ A23L 33/10 |
| WO | WO-2008076975 A1 | * | 6/2008 | ............ A23K 10/18 |

OTHER PUBLICATIONS

Boyd, B.J., Salim, M., Clulow, A.J., Ramirez, G., Pham, A.C. and Hawley, A., 2018. The Impact of Digestion is Essential to the Understanding of Milk as a Drug Delivery System for Poorly Water Soluble Drugs. Journal of Controlled Release. 2018. vol. 292 pp. 13-17.
Bluher, M. Obesity: Global Epidemiology and Pathogenesis. Nature Reviews Endocrinology. 2019, vol. 15(5), pp. 288-298.
Blundell J.E. Serotonin and Appetite. Neuropharmacology. 1984, vol. 23(12), pp. 1537-1551.
Caudill M.A. Pre- and Postnatal Health: Evidence of Increased Choline Needs. Journal of the American Dietetic Association. 2010. vol. 110(8), pp. 1198-1206.
Cutler D.M., Glaeser, E.L. and Shapiro, J.M. Why Have Americans Become More Obese?. Journal of Economic Perspectives. 2003. vol. 17(3), pp. 93-118.
Deota, S., Lin, T., Chaix, A., Williams, A., Le, H., Calligaro, H., Ramasamy, R., Huang, L. and Panda, S. Diurnal Transcriptome Landscape of a Multi-tissue Response to Time-restricted Feeding in Mammals. Cell Metabolism. 2023. vol. 35(1), pp. 150-165.
Drucker, D.J. Evolving Concepts and Translational Relevance of Enteroendocrine Cell Biology. The Journal of Clinical Endocrinology & Metabolism. 2016. vol. 101(3), pp. 778-786.

(Continued)

*Primary Examiner* — Micah Paul Young

(57) ABSTRACT

The gut-brain axis, neurobiology and neurotransmission are physiologic systems with known pathways, yet they are rarely leveraged for wellness, notwithstanding extensive literature regarding healthy diets and nutrition. Gastrointestinal (GI) evolution has equipped humans with exceptional plasticity for food abundance or scarcity, while maintaining homeostasis by producing essential neurotransmitters that drive fundamental behaviors, from seeking nourishment to engaging in routine tasks of life. The advent of cheap, abundant, and highly processed foods in the last century, however, has upended the very systems that evolved for survival with a debilitating propensity for obesity in abundance—and malnourishment where access may be limited to a scarce supply of such processed foods, or none at all. In short, a better understanding and application of physiologic signaling and equilibrium is needed in cases of weight management and malnourishment. Neurotransmitters, especially serotonin, are the primary moieties that have beneficial capacity in routine tasks, consuming but not overconsumption of needed sustenance, and achieving wellness overall. Thus, this invention provides a novel delivery mechanism of micro-dosed, natural ingredients for stimulating production of a calibrated serotonin level by leveraging the gut-brain axis through organic nutrient conversion without synthetic pharmacologic compounds. Herein, specifically engineered foodstuff that converts to serotonin (or other mediators of neurobiology) is designed to facilitate weight management and may be applied to mitigate risks of malnourishment maladies such as childhood stunting by employing directed neurobiology.

11 Claims, No Drawings

(56) References Cited

OTHER PUBLICATIONS

Dugovic, C. Role of Serotonin in Sleep Mechanisms. Revue Neurologique. 2001. vol. 157(11 Pt 2), pp. S16-9.

Fletcher P.J. and Burton M.J. Microstructural Analysis of the Anorectic Action of Peripherally Administered 5-HT. Pharmacology Biochemistry and Behavior. 1986. vol. 24(4), pp. 1133-1136.

Gafoor R., Booth, H.P. and Gulliford M.C. Antidepressant Utilization and Incidence of Weight Gain During 10 Years' Follow-up: Population Based Cohort Study. BMJ. 2018. vol. 361.

Galyean C. Levittown: The Imperfect Rise of the American Suburbs. US History Scene. 2012. vol. 13.

Hounnou, G., Destrieux, C., Desme, J., Bertrand, P., and Velut, S. Anatomical Study of the Length of the Human Intestine. Surgical and Radiologic Anatomy. 2002. vol. 24(5), p. 290.

Hui, J.Y., Harvey, M.A. and Johnston S.L. Confirmation of Ureteric Patency During Cystoscopy Using Phenazopyridine HCl: A Low-cost Approach. Journal of Obstetrics and Gynaecology Canada. 2009. vol. 31(9), pp. 845-849.

Lee, J.H., Kuhar, S., Seo, J.H., Pasricha, P.J. and Mittal, R. Computational Modeling of Drug Dissolution in the Human Stomach: Effects of Posture and Gastroparesis on Drug Bioavailability. Physics of Fluids. 2022. vol. 34(8), p. 081904.

Lindberg, L., Hagman, E., Danielsson, P., Marcus, C. and Persson, M. Anxiety and Depression in Children and Adolescents with Obesity: A Nationwide Study in Sweden. BMC Medicine. 2020. vol. 18(1), pp. 1-9.

Lopez, C., Bendix, J. and Sagynbekov, K. Weighing Down America: 2020 Update a Community Approach Against Obesity. 2020.

Lutter, M. and Nestler, E.J. Homeostatic and Hedonic Signals Interact in the Regulation of Food Intake. The Journal of Nutrition. 2009. vol. 139(3), pp. 629-632.

Pi-Sunyer, F.X. Obesity: Criteria and Classification. Proceedings of the Nutrition Society. 2000. vol. 59(4), pp. 505-509.

Pouliot, Y. and Gauthier, S.F. Milk Growth Factors as Health Products: Some Technological Aspects. International Dairy Journal. 2006. vol. 16(11), pp. 1415-1420.

Schaechter, J.D. and Wurtman, R.J. Serotonin Release Varies with Brain Tryptophan Levels. Brain Research. 1990. vol. 532(1-2), pp. 203-210.

Singh, R.B. Role of Tryptophan in Health and Disease: Systematic Review of the Anti-oxidant, Anti-inflammation, and Nutritional Aspects of Tryptophan and its Metabolites. World Heart Journal. 2019. vol. 11(2), pp. 161-178.

Spreckley, E. and Murphy, K.G. The L-cell in Nutritional Sensing and the Regulation of Appetite. Frontiers in Nutrition. 2015. vol. 2, p. 23.

Stone, T.W. and Darlington, L.G. The Kynurenine Pathway as a Therapeutic Target in Cognitive and Neurodegenerative Disorders. British Journal of Pharmacology. 2013. vol. 169(6), pp. 1211-1227.

Strasser, B., Gostner, J.M. and Fuchs, D. Mood, Food, and Cognition: Role of Tryptophan and Serotonin. Current Opinion in Clinical Nutrition & Metabolic Care. 2016. vol. 19(1), pp. 55-61.

Van Galen, K.A., Ter Horst, K.W., Booij, J., La Fleur, S.E. and Serlie, M.J. The Role of Central Dopamine and Serotonin in Human Obesity: Lessons Learned from Molecular Neuroimaging Studies. Metabolism. 2018. vol. 85, pp. 325-339.

Van Galen, K.A., Booij, J., Schrantee, A., Adriaanse, S.M., Unmehopa, U.A., Fliers, E., Schwartz, G. J., Dileone, R.J., Ter Horst, K.W., La Fleur, S.E. and Serlie, M.J. The Response to Prolonged Fasting in Hypothalamic Serotonin Transporter Availability is Blunted in Obesity. Metabolism. 2021. vol. 123, p. 154839.

Van Galen, K.A., Ter Horst, K.W. and Serlie M.J. Serotonin, Food Intake, and Obesity. Obesity Reviews. 2021. vol. 22(7), p. e13210.

World Health Organization. "Overweight and Obesity." 2020.

Wurtman, J.J. Depression and Weight Gain: The Serotonin Connection. Journal of Affective Disorders. 1993. vol. 29(2-3), pp. 183-192.

Zanchi, D., Depoorter, A., Egloff, L., Haller, S., Mählmann, L., Lang, U.E., Drewe, J., Beglinger, C., Schmidt, A. and Borgwardt, S. The Impact of Gut Hormones on the Neural Circuit of Appetite and Satiety: A Systematic Review. Neuroscience & Biobehavioral Reviews. 2017. vol. 80, pp. 457-475.

Zeisel, S.H. and Niculescu, M.D. Perinatal Choline Influences Brain Structure and Function. Nutrition Reviews. 2006. 64(4), pp. 197-203.

\* cited by examiner

CONCENTRATED NUTRITIONAL OR SUPPLEMENTAL COMPOUND FOR INTESTINAL, GUT-BRAIN AXIS AND NEUROBIOLOGICAL HOMEOSTASIS THROUGH CALIBRATED ABSORPTION INCLUDING NEUROTRANSMITTER OR ANY EQUILIBRATING COMPOUND RELEASE TO TREAT OR MITIGATE DISEASE AND CO-MORBIDITIES, PARTICULARLY OBESITY AND MALNOURISHMENT

CROSS REFERENCE TO RELATED APPLICATION(S)

This application is a Continuation-in-part of U.S. patent application Ser. No. 17/952,691, titled "CONCENTRATED NUTRITIONAL OR SUPPLEMENTAL COMPOUND FOR INTESTINAL, GUT-BRAIN AXIS AND NEUROBIOLOGICAL HOMEOSTASIS THROUGH CALIBRATED ABSORPTION INCLUDING NEUROTRANSMITTER OR ANY EQUILIBRATING COMPOUND RELEASE TO TREAT OR MITIGATE DISEASE AND COMORBIDITIES, PARTICULARLY OBESITY AND MALNOURISHMENT," filed by Brady et al. on Sep. 26, 2022

FIELD OF THE INVENTION

The present invention relates to engineered compositions of beneficial compounds, therapeutics, nutraceuticals, hormones, peptides, etc. and oral administration of low concentration therapeutic formulations with sustained release kinetics that mimic biological concentrations using steady-state pharmacokinetics delivered directly to the small and large intestines, distally when appropriate.

BACKGROUND OF THE INVENTION

A recent invention disclosure taught encapsulation of a specialized nutritional composition for overweightness, obesity and malnutrition. The composition described an engineered oral composition with biologically calibrated endurance dissolution kinetics for steady-state absorption of nutrients that stimulate low-level serotonin production via the gut-brain axis. The parent application utility had manifold applications towards weight management and privation. This filing is a continuation-in-part of U.S. patent application Ser. No. 17/952,691 with broader utility applied to the described engineered delivery composition. Conceptualizing and engineering matter release at different points in the intestinal track that timewise optimizes or stimulates circadian neurobiology can be beneficial to synaptic signaling and circulating constituents to better manage ordinary life, malady, or disease. The matter can be nutritional or therapeutic in nature with both cognitive and autosomal goals. Continuous production of a neurotransmitter, such as serotonin for mood or appetite appeasement, can provide synaptic signaling that is conducive to productivity and engagement in daily tasks and activities. Any number of peptides and/or hormones may be similarly formulated, encapsulated, and orally delivered as neurotransmitters or bloodstream constituent chemistries, as appropriate for myriad health and life functions.

Circadian homeostasis is achieved by the coexistence of complex circulating constituents delivering nutritional matter for energy and oxygen to organs amid circulating neurotransmitters, peptides, and continuous electrical impulses in physiological and anatomical harmony throughout the body. As such, hormones and other circadian constituents, such as anti-thrombin III and melatonin, can have profound effects at very low concentrations, with optimal wellbeing derived from consistent blood levels. However, dysregulation and disruption can occur as a result of myriad factors such as exhaustion, stress, sleep deprivation, malnutrition, etc.

The delivery mechanism of the composition in the continuation-in-part applies to broader compounds and utilities. The parent application described alternative compounds and materials, such as iron, whereby delivery and uptake are biologically challenging. This continuation-in-part application teaches delivery of numerous compounds that circulate in trace concentrations, which are more difficult to administer due to the minute quantities of the biologic matter. The application further addresses weaknesses associated with conventional delivery mechanisms that result in rapid release and/or abnormal spikes in the levels of delivered material that can affect interdependent biologic processes and cause system dysregulation. For example, high doses of antibiotics needed for efficacy as a function of half-life have been shown to challenge clearance organs, as well as elicit pathogenic resistance and mutation. These findings suggest therapeutic advantages from antibiotic regimens that enable even, steady-state administration.

With respect to the gut-brain axis and considerations for targeting specific regions in the gastrointestinal (GI) tract, its length is notably proportional to the size and complexity of the organism's diet. As other primates' GI tract length is approximately half that of *Homo sapiens*, one evolutionary hypothesis would follow that GI anatomy grew longer due to a more complex diet and—ultimately, distribution of the species to every continent and, consequently, nutritional milieu to sustain them. Anthropologists have described early humans living in small, organized groups of individuals that existed in general scarcity while, if any, typically consuming a singular meal, often late in the day after hours of hunting and gathering.

Notably, human intestines are similar in length, regardless of other bodily characteristics and notwithstanding certain surgical procedures (Hounnou et al., 2002). Gastrointestinal tract, small and large intestinal length and anatomy have evolved to digest complex nutritional material spanning an extended duration across a 24-hour circadian window. Many examples of nutritional matter and specific constituents like glucose have the structural integrity and stability for specialized delivery applications (e.g., alginate and chitin-coated, encapsulation, and recoating). Such protective layers can thus optimize endurance dissolution rates, delivery timing and regional targeting in the GI tract. In a preferred embodiment, intestinal transit times may be validated by combining the encapsulated delivery material with a trace chemical like peridium or glucose (measured by urine or serum analysis) and timed as a relative assay.

Specifically, the GI tract is approximately 9 meters in length and is responsible for digestion, absorption, and excretion of waste. The small intestines represent the majority of the GI tract at 6 to 8 meters long, with a vast surface area of nearly 200 square meters, which is the primary region for drug absorption. Whereas the highly acidic stomach (pH 1-2; in a fasted state) can obliterate matter and directly destroy soft mass in the digestive process. Oral pharmaceutical formulations typically compensate for these variables by elevated concentrations (above minimum levels) to ensure therapeutic efficacy. However, this strategy confers little benefit and may risk deleterious effects for acutely ill patients with compromised organ function and limited clearance capacity. However, an empty, idle, fasted stomach presents a more neutral state and initially evacuates foodstuffs, liquids and therapeutics into the duodenum (pH 6) and jejunum (pH 7) within minutes. In contrast, the presence of sufficient matter to fill the stomach can increase dwell time up to 4 to 6 hours, or longer. If consumed with a meal, prolonged acid exposure in the stomach can affect the ionization of drug molecules and impair absorption. Thus, swallowing pills or tablets while fasting limits acid exposure, especially when ingested with abundant water (pH 7). A typical compound or amount of a compound is also better distributed via a natural digestion pathway because of the massive surface area of the small intestines, regulated uptake, and assimilation framework.

Avoiding acidic stomach conditions is routinely accomplished using pH-calibrated coatings or matrices that prevent gastric enzymes and acidic conditions from degrading susceptible ingested materials such as peptides, hormones, and numerous pharmaceutical agents. However, disintegration and absorption kinetics from formulations containing pH-calibrated, enteric coatings are notoriously erratic with respect to dissolution speed and consequent small intestine transit time. However, subjecting oral medicine to digestive pathways with elevated concentrations to obtain therapeutic levels may prove unnecessary if immediately evacuated from the stomach as a micro-dosed composition comprising nutritional or therapeutic matter that can achieve uptake in the small intestines.

A preferred embodiment of a strategically engineered, endurance release composition would also enhance the efficacy and/or further optimize the use of many antibiotics, nutraceuticals, hormones, peptides, biologics, or other pharmaceutical agents through two mechanisms: First by protecting labile agents from both salivary and stomach digestive acids, allowing them to reach the small intestines; and second, by achieving linear release to replicate metabolic stasis in lieu of a bolus, or high concentration, dependent on half-life to ensure efficacy spanning a range of serum levels. Endurance release kinetics that mimic biological production would also provide a lower clearance and excretion profile, minimizing the metabolic impact on renal and hepatic function, often hampered by various disease states.

Another component of this continuation-in-part applies to specific hormones that cross the gut-brain axis to regulate hunger and satiety. Specialized enteroendocrine cells are distally located in the GI tract and help regulate hunger, absence of hunger after eating, or late-stage digestion (Drucker, 2016). These cells are specifically located in the lining of the small intestines and release hormones that act as "hunger agonists" [i.e., glucagon-like peptide-1 (GLP-1), peptide YY (PYY), and cholecystokinin (CCK)] in response to food intake, which then signal the brain to regulate hunger and satiety (Zanchi et al., 2017 and Spreckley and Murphy, 2015). Specifically, GLP-1 is produced in the distal end of the small intestines and colon by L-cells. L-cells require specific matter to stimulate natural production of the hunger agonists (Spreckley and Murphy, 2015). Distal GI-tract GLP-1 production is consistent with perceived satiety from naturally fibrous and complex foodstuff available prior to industrial food processing methods, whereas circadian rhythms (neurobiology) have remained largely unchanged from prehistoric biology. Evolutionarily, late-day stimulation of distal GLP-1 production from complex and difficult-to-digest fiber and carbohydrate matter may have been critical to human survival by assuaging hunger sensations to allow migration while working to hunt or gather the next meal.

Diets increasingly comprised of highly processed foods—and readily accessible products consumed throughout the day—can nonetheless fail to stimulate the entirety of the GI tract, with a majority of such foodstuffs being digested in the first half of the small intestines without reaching distal bowel region. Whenever glucose, calcium or other nutrients are absorbed without reaching the L-cells—in the absence of unabsorbed dietary fiber and carbohydrates, they remain dormant, thereby limiting GLP-1 production and release that signal perceived satiety.

The need for nutrients to traverse these anatomical characteristics appears to contravene practices intended to achieve "fullness" and mitigate hunger by consumption of several small meals throughout a circadian period. Conversely, a single, nutritionally and structurally complex daily meal that prolongs digestion and facilitates nutritional delivery to the distal bowel to trigger appetite-regulating hormone production would be more consistent with GI anatomy. The approach of aligning a single meal with circadian biology has been studied in numerous model organisms and has been shown to beneficially influence and reshape gene expression in the body and brain of rodents (Deota et al., 2023). However, current obesity demographics reflect profound challenges overwhelming the public health community, as myriad alternatives to this anatomical and circadian approach—from food exclusions to portions to protein supplementation, to liquification—have had no impact on the global trajectory of a burgeoning epidemic.

Epidemiologists consider the obesity epidemic a public health crisis which is exacerbated by the ubiquity of energy-dense, hyperpalatable food that drives overindulgence and overwhelms evolutionary homeostasis (Blüher, 2019). Obesity is diagnosed when an individual's body mass index (BMI) exceeds 30 ($kg/m^2$), with BMI of 25 or greater categorized as overweight (Pi-Sunyer, 2000). In 2020, more than 2 billion adults (39% of the global population) were clinically considered overweight; of these, 600 million were classified as obese (WHO, 2020). The condition results in excess body fat accumulation that negatively affects most metabolic systems with associated risks and predisposition to an array of diseases (comorbidities). Globally, the economic impact of obesity from related health care, reduced life expectancy, disability and lost productivity costs has been estimated at nearly $1.4 trillion (USD) (Lopez et al., 2020).

While dietary and some surgical interventions represent the cornerstones of obesity treatment, most approaches have fallen short and remain widely debated among health professionals and the general public. Adolescent obesity is particularly associated with psychological disorders including depression, anxiety, and despair, which often leads to invasive bariatric procedures (Lindberg et al., 2020) for those with the means and access to such interventions. Given that weight loss is typically a gradual process, a key limitation to successful dietary intervention is the relentless risk of diminished patient resolve. Effective weight loss dietary strategies can thus require biological and psychological habituation. Yet, most solutions have remained elusive due to cost and/or limited access to invasive procedures; whereas, dietary approaches routinely challenge patient determination. These factors are increasingly common among lower-income communities and most prevalent in emerging countries.

Biochemically, minor imbalances (e.g. impact of irregular sleep patterns on leptin and ghrelin, hormones that drive perceived appetite) can drive significant metabolic changes and lead to excessive weight gain. Morbid obesity is a recent phenomenon circumspect to post-World War II industrialization and a surfeit of readily accessible, often processed, and not always nutritious, foodstuffs that can overwhelm circadian neurotransmitter systems that evolved under conditions of intermittent access to nourishment (Cutler et al., 2003; Galyean, 2012). As circadian biochemistry remains relatively unchanged, the capacity to compensate for overeating has not similarly evolved. However, GI neurobiology has established circadian rhythms that are typically manifested in the synthesis of proteins and peptides that automatically regulate physiologic systems throughout the body—and throughout the day. Notably, neurotransmission of serotonin and oxytocin occurs throughout the body and particularly the GI tract, sending critical metabolic signals to the brain and in turn, stimulates conscious perceptions including fullness or hunger, energy or fatigue, and related conditions.

The human body requires relatively minimal nutritional extraction given nutrient variety, complexity, and volume of indigestible matter. If variety and/or complexity are lacking, however, additional mass is required. The gastrointestinal tract thus accommodates such variables spanning nutrient assortment, food scarcity and abundance, and cognitive caloric fuel requirements. Thus, the digestive system had notably adapted to foodstuff privation and abundance with only rare instances of obesity prior to recent sociological and dietary shifts in work patterns and processed food abundance and access.

When such foods are readily available in societies where specific meals are traditionally consumed, continuously eating can occur in response to stomach emptying. The stomach serves as a highly acidic, transitional organ that aids absorption by optimizing digestion before emptying. During a fast, however, ingested material is quickly transferred to the small intestines. This transfer results in a short-lived, rapid spike in the neurochemical milieu created by the small intestines and communicated to the brain. Such spikes and falls can result in a cycle of overeating relative to basal caloric requirements. Similar responses occur at usual meals; whereby the combination can lead to weight gain and ultimately, obesity.

Given that neurotransmitter processing and stimulation are accomplished in the small intestines and thus, minimal stomach involvement is required, wellbeing and weight management may be achieved via routinely longer fasting periods with as little as a single daily meal. This is also known as "intermittent fasting." Beyond volume, a truncated eating period requires nutritional variety to fuel intricate biological functions, as well as satisfy the psychological complexities associated with taste and texture. However, adherence to such regimens is challenging and often stressful. In the parent patent, novel innovation that bridges gut-brain axial signaling is aimed to facilitate dietary interventions for weight management via imperceptible neuropeptide signaling.

Prefrontal cortex activity is diminished during fasting, which regulates brain functions such as logic, reasoning and planning, as evidenced by fMRI analysis (Van Galen et al., 2021). This region also helps curb impulses associated with appetite and food cravings. During a fast, these activities shift from the prefrontal cortex to the limbic system (i.e., hypothalamus, thalamus, and nucleus accumbens) which can stimulate perceptions of hunger. The transition from prefrontal to limbic activity is associated with behavioral responses to the biological requirement for sustenance and perceptions of food scarcity conditions.

Specifically, the neural framework associated with the gut and the brain that regulates eating behaviors can be manipulated to control appetite. The brain, particularly the limbic region (i.e., hypothalamus) plays a crucial role in modulating food intake by sensing molecules and metabolic signals. Post-ingestion, intestinal absorptive sites stimulate neural pathways that mediate the transmission of nutritional signals from the gut to the brain and elicit perceived wellbeing or equilibrium. Principally, food intake is controlled via two brain mechanisms or circuits (Lutter and Nestler, 2009): The homeostatic circuit matches energy intake and output, and a "hedonistic" pathway that drives reward mechanisms, both of which are linked to serotonin (Van Galen et al., 2021).

Serotonin is a monoamine neurotransmitter that also acts as a hormone and carries essential messages between nerve cells in the brain and throughout the body. The fundamental role of serotonin in food intake, mood, and other circadian patterns (e.g., sleeping) has been well researched and characterized (Wurtman, 1993; Dugovic, 2001; Strasser et al., 2016). As brain serotonin production is modest, up to 90% of endogenous serotonin production that occurs in the GI tract is required. By enabling synaptic communication between the brain and the gut, serotonin plays a critical role in numerous circadian functions. However, maintaining serotonin levels is delicate, and imbalances can be deleterious, often associated with selective serotonin reuptake inhibitors (SSRI) and serotonin blocking therapeutics (Koyuncu et al., 2012).

Designing a serotonin regulating supplement to curb brain impulses arising from neurochemical imbalances could achieve homeostatic levels of serotonin, resulting in a relative state of psychological equilibrium. Steady-state, trace serotonin production that emanates through the gut-brain axis could thus achieve homeostasis. Due to characteristic rapid stomach emptying, a supplement can be engineered to pass through the stomach and duodenum intact. As such, foodstuff designed for absorption exclusively in the small intestines holds functional advantages with respect to weight loss. The process would enable prolonged, calibrated delivery to result in greater digestive energy expenditure than caloric absorption; and conversely, more easily digested energy requirements for faster assimilation.

As such, neuro- and circadian biology can be leveraged to effect weight loss and establish a healthy BMI. While it might appear antithetical to use nutritional intake to achieve a healthy BMI, the parent invention drives a circadian cycle of serotonin stimulation to achieve caloric homeostasis to facilitate adherence during weight loss while mitigating anxiety. Accelerated absorption can also be calibrated for treatment of malnourishment.

For weight management, a compressed, calorie-dense tablet or capsule would thus increase compliance and afford convenience. By requiring more calories for absorption than caloric content, the net effect is to shift digestion dynamics, such as intestinal peristalsis, surface or contact area exposure and enzyme production and utility. The parent invention takes advantage of the gut-brain axis, neural connections between the enteric nervous system of the small intestines and the central nervous system, nutrient digestibility, neurotransmitter stimulation, gastric emptying and transit times. It also provides a novel delivery form that produces steady serotonin flows to the brain using natural foodstuffs, compression, and/or coatings and administration to bypass initial stomach digestion for absorption entirely inside the small intestines. Ingestion of one or more doses during a fasted state would provide a method for sustained serotonin signaling and psychological equilibrium.

The use of low energy dense foods that impart significant volume to the stomach and GI tract resulting in overall reduced caloric intake have been previously described. For example, U.S. Pat. No. 5,336,486 describes a vegetable fiber that induces satiety via filling the stomach. In addition to compliance issues, these methods are associated with GI discomfort and flatulence produced by gut microbiota. To counteract volume expansion issues, the use of easily digestible products with minimal caloric density have also been described in U.S. Pat. Nos. 5,063,073; 5,654,028 and 6,426,077. Additionally, the use of collagen-based biopolymers and gelatin formed into hydrophilic powders, granules or pellets with poor absorption kinetics have been previously explained in U.S. Pat. No. 6,103,269. The use of porcine gelatin capsules that contain absorbent hydrogel particles designed to form a three-dimensional bulk matrix in the stomach was described in U.S. patent application Ser. No. 15/942,655. The prior art associated with these inventions has thus relied primarily on physical mass and low-calorie, poorly digestible compositions that simulate sensations of satiety, hence give rise to poor compliance in the absence of actual nutrients. The object of the present invention is not associated with vegetable fibers, biopolymers or hydrogels that induce satiety by filling stomach volume.

U.S. Pat. No. 8,562,952 describes a method of inducing satiety via a serotonin receptor agonist, serotonin re-uptake inhibitor, or serotonin. The patent describes suitable compositions of peptide YY (and functional analogs), calcitonin gene-related peptide, an adrenergic agonist, an opioid agonist, or combinations thereof. Addition of an active lipid may be used to prolong GI dwell time to enhance dissolution, bioavailability and absorption. The parent invention differs from the previous art in composition, does not include peptide YY, calcitonin gene-related peptide, an adrenergic agonist, an opioid agonist, nor is the use of an active lipid required.

Derived from natural ingredients, such as those in chicken eggs and cow's and/or goat's milk—or plant-based proteins in alternative embodiments, the composition of the parent invention is a novel delivery mechanism for organic nutrients, and not synthetic molecules. The mode of action associated with the parent invention deviates from the current art associated with system suppression, restriction, indigestible bulk, and physical manipulation for weight management.

The parent invention employs strategic engineering of micro-dosed nutrients that alter the delivery pathway to influence brain function without caloric density. The parent invention further provides a method and composition that quickly evacuates the stomach, feeds the small intestines and by extension, the brain, via the gut-brain axis. This affords a calibrated stimulation of serotonin from micro-absorption of essential nutrients using intense intestinal peristalsis and energy, resulting in a net negative calorie ingestion and neural and psychological stasis. This continuation-in-part application expands delivery compositions to comprise additional compounds including, but not limited to, antibiotics, nutraceuticals, hormones, peptides, biologics, or other pharmaceutical agents.

Gut-derived neurotransmission and nutrition delivered in low concentrations can mimic natural biology via capsules compounded to enable effective biological uptake, facilitate normal homeostasis, and optimize circadian bio-regularity. This invention would stimulate synaptic (gut-derived serotonin) and gut-brain axis signaling consistent with postprandial, circulating constituent serum levels; whereby cellular processes would signal a steady-state of wellbeing. Dysregulation occurs when constituent chemistry is perturbed, causing numerous responses including: glandular osmotic increases, dyspepsia, perspiration, nausea, insomnia, fatigue, etc. This invention delivers a natural method of gut-derived serotonin as a neurotransmitter. The absorption kinetics of the composition can also deliver compounds at physiological and/or desired therapeutic levels in lieu of bolus dosing and empiric administration. The functional composition of naturally derived matter (i.e., lyophilized and compressible milk and egg) that matches mammalian evolution, while also suitable for industrial production, is more effective, less expensive, and easier to administer than other ambulatory and sentient patient delivery methods, including that of parenteral or IV drip.

BRIEF SUMMARY OF THE INVENTION

This continuation-in-part application provides a novel oral delivery composition in a solid form administration (e.g., tablet, capsule, pellet, granule, etc.). The parent application is comprised of micro-dosed, low-volume and nutrient dense egg and milk formulated to bypass stomach digestion processes. The composition of the parent invention modulates serotonin production in the brain and is useful for appetite management and treating nutrient deficiencies such as those associated with stunting. In some instances, the present invention may be useful for surgical preparation and post-operative recovery or during potentially debilitating treatment routines.

The composition of this continuation-in-part application would improve oral delivery methods and achieve specified dosage administrations that mimic natural biologic functions, like steady state delivery employing calibrated, intravenous drips using preferred administration methods. Oral delivery is the most common route for drug delivery due to ease of use, non-invasiveness, and convenience for self-administration. However, oral drug delivery is challenging due to complex pathways and disparate metabolic factors that affect drug solubility, stability, permeability and absorption.

Compacted into a dense, solid tablet, the invention can be ingested without chewing. When taken at least 2 hours after eating, the enteric coating would be dissolved only upon transfer to the small intestines (pH and peristalsis driven), without stomach processing, nutrient modification or loss from inertial forces that grind and mix disintegrated contents prior to passing through the pyloric sphincter. Notably, while empty, stomach muscle contractions are minimal until a myoelectric complex rapidly stimulates evacuation of its contents. Thus, with rapid delivery of the invention to the small intestines, the GI contraction, torque and crushing forces would then allow for calibrated absorption. Given optimal transit time of ingested material and associated energy (caloric) consumption from peristalsis, an extended, continuous stimulation of serotonin production would thus promote psychological equilibrium.

However, meal timing and nutritive density of consumed foods can impact stomach emptying, which is necessary for this invention to promptly transfer to the small intestines. In turn, while leaning towards the right side can accelerate transfer to the small intestines (Lee et al., 2022), it would not be sufficient to ensure the intended use of this invention. As most absorption takes place in the small intestines, gastric emptying times would thus represent a rate-limiting step in delivery. The gut-brain pathway is calorie independent, and while the composition of the parent invention is nutritive, more calories would be expended than consumed. That is, the delivery of intact, compressed nutrient tablets to the small intestines, without significant stomach breakdown, would thus require digestive processes that require more metabolic energy than contained in the tablets.

The parent invention further embodies a preparation of proteins and micronutrients found in eggs and milk with distinct biologic properties. Eggs obviously facilitate reproduction and provide nutrition from conception to hatching, and milk is easily digestible (with lactose neutralization for many adults), while providing cognitive and immune support. When lyophilized, the stability and therefore, shelf life, of these materials are superior to most supplements and foodstuffs, which can also provide commercial and storage advantages that help ensure the integrity of these ingredients.

Beyond weight management, the composition of the parent invention has potential malnourishment applications. The benefits could ease food security challenges, which have been exacerbated by climate change impact on agriculture and viable grazing access. Traditionally, wheat, maize and flour are commonly distributed to fight hunger. While grain has been historically considered a food staple with various essential vitamins, these carbohydrates are nonetheless lacking in other critical nutrients. The parent invention could thus provide a supplement to such practices with complementary sustenance.

In this continuation in part, delivery of carbohydrates and lipids in a specially engineered oral composition would deliver critical nutrient signals to targeted regions in the GI-tract. Given that GI-tract length is relatively consistent among individuals, and as the small intestines are the longest portion (6 to 8 meters in adults) and the predominant site for nutritional uptake, specifically engineered oral configurations can enable uniform timing for release. Notably, the ileum is 1.5 to 1.8 meters long and the last segment of the small intestine located between the jejunum and the large intestine, comprised of the colon, rectum and anus.

In one embodiment, distal ileum and colon delivery of nutrients required for L-cell stimulation and subsequent GLP-1 production represents a natural and cost-effective alternative to this class of therapeutics. GLP-1 production occurs primarily in the ileum and colon, where L-cells are found throughout the lining and in the submucosal layer, respectively. When intact carbohydrates and lipids reach the ileum and colon, L-cells are stimulated to release GLP-1, which circulates and binds to its receptors to establish the gut-brain signaling. GLP-1 plays a critical role in regulating glucose metabolism, appetite, satiety, and gut motility. While requiring significant reimbursement, novel subcutaneous and oral GLP-1 receptor agonist drugs synthetically accomplish this signaling but have been shown to elicit a rebound effect when used off-label for obesity (e.g., Ozempic; active ingredient: Semaglutide; approved for the treatment of Type II diabetes). In other examples, evidence of dysregulation with thyroid and insulin-dependent patients can have life-threatening consequences. Insulin implant pumps have been marginally successful and require strict patient selection, while not all patients achieve consistent thyroid regulation with available approaches.

Another vital, yet delicately balanced peptide is serotonin. The body produces serotonin in the brain (raphe nuclei) as well as from conversion of tryptophan upon consuming and transferring nutrients to the GI tract (enterochromaffin cells). In these pathways, the brain stem raphe nuclei produce 8 to 20 milligrams of serotonin per day, depending on the individual's age, diet and activity level; whereas the GI enterochromaffin cells typically generate and release 500 to 1,000 milligrams of serotonin per day. These dynamics suggest that orally ingested molecules can thus be directed without damage or modification from the stomach to the GI-tract via optimized oral delivery mechanisms that mimic natural homeostatic processes.

DETAILED DESCRIPTION OF THE INVENTION

The materials, compounds and composition described below are to be considered exemplary and explanatory, but not limiting. The parent invention relates to tablets prepared from a blend of eggs and milk, and optionally additional binders, excipients, or fillers that are engineered for release in the small intestines to stimulate serotonergic signaling. The materials are stepwise metabolized by the gut microbiota into indole and indole derivatives and subsequent synthesis by enterochromaffin cells to produce serotonin. In alternative embodiments, it would be obvious to include additional beneficial ingredients or other advantaged chemistry to the composition, such as folic acid, formulated to support planned pregnancy. This continuation-in-part application teaches that a strategically engineered, endurance release composition for delivery of antibiotics, nutraceuticals, hormones, peptides, biologics, or other pharmaceutical agents would enhance their efficacy and/or further optimize their use.

The active ingredients of the primary embodiment of the parent invention comprise lyophilized chicken eggs and cow's and/or goat's milk. The material form of these active ingredients demonstrates compatible tableting substances with robust shelf stability. The constituents are accessible and affordable, representing ideal raw materials for diverse applications and populations. The parent invention utility is focused on human weight and nutritional management; however, embodiments could be adapted for domesticated or wild species.

The essential macronutrients in eggs support numerous biological functions, including nutritive molecules that act as precursors, required for cell division, growth, membrane signaling and brain function (Caudill, 2010; Zeisel & Niculescu, 2006). The protein profile of the egg matches human dietary requirements and contains all non-essential and essential amino acids. In addition to protein, the fatty acids of egg yolks (in particular, DHA) are likewise vital for cognitive, neurologic, and optical sustenance.

Milk is a mammalian-derived emulsion of oil in water that contains bioactive proteins, lipids and saccharides, as well as antibodies, enzymes, antimicrobial peptides, oligosaccharides and hormones (Pouliot and Gauthier, 2006). Thus, milk provides energy, essential amino acids, fatty acids, vitamins, and diverse inorganic elements. Like eggs, milk proteins include all essential and non-essential amino acids, as well as caseins and whey protein with rich nutrient value and high digestibility for efficient absorption and utilization. Uniquely, lactose [$\beta$-d-galactopyranosyl-(1→4)-d-glucose] is a carbohydrate and the most abundant component by weight in lyophilized milk. Lactose has low hygroscopicity, physical and chemical stability, and water solubility properties that have led to wide utilization as an excipient binder in tablets. The inclusion of lactose during compounding optimizes viscosity, compaction, and bulking density properties. Depending on the tablet manufacturing method and release characteristics, inclusion rates of lactose vary from 30% to over 50%, which can offset other active ingredients. As lactose is a key constituent of lyophilized milk, dosing strategies can be controlled without supplemental excipient requirements, thus conferring additional benefits to tablet formation of the present invention. The composition of lyophilized milk creates an excellent nutritional source for infants that is digestible, well tolerated, and optimized for efficient nutrient uptake during the first year of life. As such, it may also be readily optimized for GI maturation stages from neonates, to infants, children, adolescents, adults, seniors and the infirm of any age.

In an alternative embodiment, a vegan substitute with a suitable amino acid profile may be preferable. Such substitutions may include chia seed protein, hemp protein, pea protein, pumpkin protein, rice protein, soy protein, sunflower protein, or other plant-based source containing tryptophan. In yet another alternative embodiment, the user may have an intolerance to egg and/or milk products. In the case of milk (lactose) allergies, the tablet can be formulated to contain lactase enzymes to aid digestion. While egg allergies are often outgrown in the first five years of life, some infants and adults may have adverse reactions to the egg albumin, yolk or both. Thus, a modified dosage comprising a higher concentration of lyophilized milk or a combination of lyophilized milk and another suitable plant-based protein may be preferred.

Food is not only necessary as metabolic fuel for the body but has a profound role on brain function, which is not typically considered when evaluating diet for weight management. Tryptophan is essential for human life but is not biologically synthesized. The majority (>90%) of ingested tryptophan is converted into biomolecules for neurological signaling (Strasser et al., 2016). The amino acids in eggs and milk include significant levels of L-tryptophan compared to other foods (Singh, 2019). Tryptophan is a precursor for serotonin, a known peripheral satiety signal that acts through the afferent vagal nerve pathway (Schaechter and Wurtman, 1990).

The serotonergic system of the brain and GI tract play synergistic roles in the control of food intake and whole-body energy homeostasis. Over-stimulation of serotonin production can cause negative side effects as reported with administration of some pharmaceuticals that alter biologic levels. Increased administration of serotonin precursors (i.e., tryptophan rich foods) has also proven ineffective, because serotonin must compete with other large neutral amino acids (LNAA) to cross the blood-brain barrier (Stone and Darlington, 2013). Typical of foodstuffs with diverse amino acid profiles, the net effect of tryptophan is notably lost when excess LNAAs are also present. The micro-dosed, solid composition of the present invention combines balanced tryptophan concentrations with extended release of serotonin production stimulants directly to the absorptive sites of the small intestines.

The process of satiation, or perceived indifference to eating, can be mediated by serotonin-containing neurons and pathways, as evidenced by pharmacological manipulation with serotonergic drugs (Blundell, 1984). Studies of receptor blocking, systemic administration (of serotonin) (Fletcher and Burton, 1986), use of selective serotonin reuptake inhibitors (SSRI) (Gafoor et al., 2018) and molecular neuroimaging (Van Galen et al., 2018) have characterized the role of serotonin signaling in eating behavior and long-term weight regulation. In the primary embodiment of the present invention, a solid composition, or tablet, would be administered and engineered to rapidly evacuate the stomach. It would then stimulate calibrated, trace serotonin production in the small intestines into the bloodstream to induce psychological equilibrium, which can facilitate extended fasting between meals.

In the present invention conforms to circadian rhythms that require homeostasis relative to periods of rest and activity. This aspect is imperative due to the complex neural network of the GI tract that influences cognition, mood, stress, decision making, and perceived well-being. System stability or homeostasis can be achieved through the formulation, dosage, timing and delivery mechanisms described in this patent. The relative concentrations of serotonin-stimulating amino acids of the present invention are calibrated and formulated to avoid competitive inhibition, excessive hormone stimulation and negative biologic disparities.

In the primary embodiment of the invention, the tablet composition is directed towards achieving equilibrium with respect to brain stimuli that govern homeostasis and cognition. The composition is manufactured free of disintegrants typically employed in tableting processes. As such, disintegrants are used to facilitate rapid breakdown and provide immediate release or delivery of active ingredients. Whereas inclusion of disintegrants would impact serotonergic signaling from a synaptic response immediately after ingestion. The preferred use of the parent invention is directed to stimulate continuous, low-level serotonin signaling between the gut-brain axis.

Alternatively, in another embodiment, the tablet would deliver dense nutrients to treat deficiencies and maladies caused by chronic conditions of hunger (e.g., stunting) and as a healthcare supplement during debilitating or potentially toxic treatment (e.g. radiation and chemotherapy). As it is essential to ensure an individual's robustness to endure any intervention, administration could be applicable prior to such procedures or as a presurgical supplement to boost vigor and aid recovery. The composition of such an embodiment would be similar, however, dosing regimens, concentrations, frequency, and timing would vary depending on individual or therapeutic requirements. In such alternative embodiments for use beyond weight management, the inclusion of a disintegrant may be beneficial to facilitate faster absorption and nutrient uptake.

Traditional tablet manufacturing requires the use of filler agents or excipients that create intergranular bonds and fuse the materials together to impart tensile strength. Common binders include cellulose derivatives, gelatin, polyvinylpyrrolidone, starch, sucrose, and zinc stearate. The active ingredients of the invention contain lactose, which is also an established binding additive and would obviate the need for additional binding agents. However, a compression lubricant to prevent tablet cracking and allow for smooth ejection after compression may be used to prevent the lyophilized material from sticking to the compression die or punch. Common lubricants include calcium stearate, magnesium silicate, magnesium stearate and stearic acid. In the preferred embodiment, magnesium stearate, a metallic salt boundary lubricant, is used for tablet formation due the material cost, lubrication capabilities, high melting point and chemical stability.

In the preferred embodiment of the invention the tablet can be formed in different sizes. According to Food and Drug Administration (FDA) recommendations for swallowing, the overall size of the tablet should be no larger than 22 mm. The typical tablet range for the preferred embodiment is 1 to 22 mm, depending on the concentration of the ingredients. Given the lack of binders, fillers or excipients required for tableting, dosing is not compromised by size. Should smaller tablets be desired, ingredient concentration and frequency may be varied accordingly. In alternative embodiments, it would be obvious that the tableted lyophilized material described could be encapsulated in an alternative container designed for oral administration.

The tablet may be compressed or molded in a variety of shapes, sizes and weights, and the delivery form is preferably solid. Common tablet geometries include round, oval, oblong, square, rectangular, diamond, triangular, pentagonal and a core rod. In the preferred embodiment of the invention, the tablet is oblong, which can facilitate swallowing by optimizing length, width and thickness. In alternative embodiments, the tablet may be formed in layers or segments that disintegrate at different rates. The calibrated dose of the preferred invention is thus based on tablet size, geometry, and specific use, whereby frequency and quantity can be varied.

In a preferred embodiment, the invention is intended for oral administration on an empty stomach. While oral consumption is preferable in terms of compliance and cost, the delivery method faces several challenges during transit through the GI tract. In the primary embodiment of the present invention, tablets are enterically coated to protect against digestive acids in the gastric juices of the stomach and ensure intact transfer to the small intestines. The enteric coating on the tablet may comprise of polymers and copolymers such as butyl stearate, carnauba wax casein, cellulose acetate, ceresin, dextrin phthalates, ethyl acrylate, hydroxypropyl methylcellulose, keratin, methacrylic acid, methyl methacrylate, methyl phthalyl cellulose, paraffin, shellac, or another copolymer of anionic character. The enteric coating polymer can be the same or different from any polymer in the protective coating and can be one or a combination of polymers and/or copolymers. The enteric coating that protects the tablet from stomach acids can vary between tablet layers, and individuals with stomach-emptying abnormalities (e.g., complications of duodenal ulcers) may require additional coating strategies to benefit from this invention.

Amino acid absorption in the small intestines does not require pre-digesting in the stomach. In the present invention, timing of tablet administration and engineering are essential to facilitate rapid stomach evacuation through the upper anastomosis and into the small intestines, thereby allowing for adequate time and exposure to the small intestines to optimize nutrient absorption. Notably, the membranes in the small intestines are far more permeable than those in the stomach.

The rate at which matter passes through the stomach and GI tract determine the ultimate absorption of the ingested material. Delivering these compounds through a tablet metabolized in the small intestines provides greater nutrient uptake and utilization. In the present invention, physiological balance and psychological equilibrium from continuous trace serotonin stimulation avoid the spikes and drops typically caused by randomly eating throughout the day, likewise imparting mood neutrality, and a perception of wellness. This invention thus facilitates optimal food intake when subliminal stimulation of serotonin levels and gut-brain neurotransmitters are calibrated to achieve homeostasis.

In a preferred embodiment, the coated tablet bypasses stomach pre-digestion followed by measured GI disintegration to allow for sustained, gradual absorption and signaling between the gut-brain axis. The protective coating is degraded upon transfer to the small intestines, thus delivering the compacted active ingredients. In the intestines, mechanical forces and torques applied by peristaltic contractions aid disintegration and disaggregation and allow for dissolution of the lyophilized egg and milk. Disintegration is stepwise due to compaction of the material; thus, granules are first produced and more slowly disaggregated, resulting in fine particle formation. A single tablet can reside in the small intestine for as long as four hours or more, as surface area is slowly increased by the muscular activity of the intestines.

The FDA defines tableting and capsule coatings and formulations with respect to immediate release, extended-release, delayed-release, or sustained-release, which are accomplished by the compound or compounding of the material. Typically, this is accomplished through the application of a coating material with pH resistance, and/or addition of a commercially available hydrophilic matrix or suitable binder material. Given that gastric emptying times, pH levels and numerous oral/GI biological factors are highly variable from patient to patient, oral administration based on compounding can be disadvantaged. The proposed invention is nonetheless intended for administration after stomach emptying and engineered to allow continuous peptide release and neurobiological stimulation in the small intestines when applied to weight management. Exposing orally administered matter to stomach acids for unpredictable periods can diminish efficacy, uptake, bio-assimilation, predictability, delivered dosage, and can also alter or change the structure and compatibility of the material. Current enteric coatings may delay the decomposition of a delivered agent by resisting harsh stomach acids, but absent compacting as applied in this invention, these coatings would not control release rates upon intestinal transfer to the same degree.

A primary aspect of the present invention is tablet design to ensure appropriate, sustained delivery in the small intestines for optimal digestion and controlled biochemical stimulation. In one embodiment of the present invention, the tablet is formed by compacting a powder blend in a die and punch tooling system. The compression force of the tooling system is between 10 (99.6 kN) to 100 (996.4 kN) tons. Tablet compacting can be performed under vacuum with or without in-line cooling. In the primary embodiment of the invention, the powder blend includes defined percentages (by weight) and ratios of lyophilized egg and milk protein, wherein the lactose composition of the lyophilized milk serves as the meltable binder. Optionally, another suitable binder may be added to the powder mix to increase matrix bindings. In some embodiments, a suitable lubricant may be added to the powder to aid in tablet formation and ejection during manufacturing. In the preferred embodiment of the invention, no engravings or special features that would alter compaction are etched onto the tablet.

In an alternative embodiment of the parent invention, lyophilized eggs and milk would be encapsulated in alginate microspheres—in lieu of compression, to calibrate absorption. The pKa of the alginate microspheres are stabilized by intermolecular hydrogen bonds that are easily broken in the intestinal fluid but remain stable in gastric fluids. The microencapsulated, lyophilized egg and milk alginate complexes are formed via freeze drying. Spray dried, lyophilized egg and milk powder form a uniform, fine particulate powder of approximately 5 microns. The calcium containing spray-dried material is subjected to reverse spherification to create a hard outer shell formed by the cross-linking reaction of alginic acid and calcium. Spray drying is a cost-effective, scalable technique to create uniform encapsulated material.

In a similar embodiment, the lyophilized egg and milk material are combined with alginate and vigorously mixed. The solution is forced through an orifice under high pressure and passed through an atomizer to create cross-linked microspheres that have a dense calcium-alginic acid outer shell containing a liquid core comprised of the constituent parts of the lyophilized eggs and milk that remain uniform while encapsulated by, but not incorporated into, the crust of the sphere. After microspherification, the material can be dehydrated or subjected to freeze drying. In some embodiments, the freeze-dried microspheres are subjected to a second alginate coating, which may comprise a defined concentration of individual microspheres created in the previous step. The resultant material may be exposed to a second freeze-drying procedure and then subjected to traditional tableting and enteric coating processes. The concentration of alginate can be varied to tailor shape, viscosity, aspect ratio and the interfacial tension of the formed microspheres.

In various embodiments of the preferred invention, the inclusion of phenazopyridine hydrochloride may be added to the composition for digestion analysis and quality control. This over-the-counter active ingredient is a poorly soluble dye routinely used to alleviate the symptoms of urinary tract infections and impart a reddish-orange color to the urine. During manufacturing, phenazopyridine can be added to specific layers, incorporated into the core, mantle or surface of the tablet. The dye can be easily visualized by examining urine color change as early as 20 minutes, but within one hour after ingestion (Hui et al., 2009). Analysis of urine characteristics in this embodiment may thus be used to confirm initial tablet disintegration and dissolution in the small intestines.

In the present invention, the tablet is intended for administration on an empty stomach to facilitate rapid transfer to the small intestines caused by fasted state metabolic spikes that enable gastric emptying. The tablet contains multiple layers of protection that both stabilize the lyophilized material and prevent breakdown in low pH environments. After transfer to the small intestines, the enteric coating is degraded, and the compressed spray dried alginate microspheres and dual layer alginate microspheres are slowly disaggregated by peristaltic contractions. Individual microspheres are then disintegrated to release encapsulated materials, either small spheroid substances (dual encapsulated) or lyophilized milk and egg constituent parts and amino acids into the small intestines for uptake. The dwell time of the material can be customized depending on the percentage of alginate, the degree of spherification, the formed layers, dual encapsulation methods and particle size to tune release kinetics of the material.

Extended duration pharmacological methods are typically based on administration pathways and not specifically engineered for controlled intestinal uptake over time. Time-release encapsulations are commonly engineered coatings of bolus dosages that avoid stomach acids to facilitate delivery to the small intestines—and in some cases, to maintain molecular integrity otherwise lost in gastric fluids. Similarly, liposome encapsulation is typically applied to delayed bolus administration as opposed to uptake dependent on peristalsis and digestion. This invention calibrates dosages over time by slowing the dissolution for prolonged absorption. The invention would therefore be obvious and suitable for delivery of therapeutics where micro-dosing and calibrated release or sustained dosing would be beneficial (e.g., iron supplementation, other neurotransmitters, pharmaceuticals, vitamins, supplements, foodstuff, or nutraceuticals, including micronized sustenance for privation and malnutrition).

An additional feature of this continuation-in-part is an endurance release system or steady-state delivery, wherein the compound is compacted to withstand intestinal peristalsis. As a convenient oral composition, the embodiment of compacted material could also incorporate endurance release components to deliver therapeutic or nutrient constituents at a slower rate and over a longer period to mimic normal metabolic production, resulting in trace concentrations (e.g., picogram quantities) that are released into the bloodstream over time.

This preferred embodiment also combines compression of material into an ingestible form (i.e., tablet, capsule, etc.) with administration on an empty stomach. Thus, with limited dwell time and transfer through a relatively neutral stomach, it is rapidly transferred into the intestines, and mechanically and metabolically processed via intestinal peristalsis.

Upon reaching the small intestine, the embodiment delivered by oral ingestion and through an empty stomach would also mimic IV fluid delivery of drip or pump-calibrated concentrations directly into the bloodstream. Hormone examples with exceptional utility would include pancreatic or thyroid peptides; whereby current delivery methods have achieved glandular release with limited success.

In the preferred embodiment, delivery of intact carbohydrates and lipids in a specially engineered milk and egg oral composition would deliver critical nutrient signals to precise regions in the GI tract, such as the distal ileum and colon, for L-cell stimulation and GLP-1 production.

In this continuation-in-part, the inclusion of peptides, hormones, nutraceuticals, antibiotics or other pharmaceutical agents and biologics are added to the composition for oral delivery of endurance release and compacting mechanisms that limit exposure in the stomach and deliver a steady-state of trace levels of the agents directly to the small intestines. The endurance release thus mimics natural and biological production over extended periods of time. In particular, co-administration of milk with relatively insoluble compounds has been shown to be beneficial to solubilization and digestion (Boyd et al., 2018). The lipid content in mammalian milk comprises over 95% triglycerides, which form colloidal, liquid crystalline structures that typically optimize drug solubility. Therefore, co-administration of a therapeutic delivery agent with lyophilized milk and egg materials would thus provide essential lipids, protein and carbohydrates that enhance bioavailability while limiting exposure to stomach acids with immediate delivery to the small intestines.

What is claimed:

1. An extended-duration, solid form oral and enterically coated dosage that enables low concentration and steady state delivery of a therapeutic drug, biologic, hormone, peptide, or another pharmaceutical agent consisting essentially of:
   a. Alginic acid encapsulated lyophilized whole egg powder;
   b. Alginic acid encapsulated lyophilized whole milk powder;
   c. One or more therapeutic drugs, biologics, hormones, peptides, or other pharmaceutical agents;
   d. in a pharmaceutically acceptable enteric form containing a protective coating;
   wherein the solid form dosage is taken on an empty stomach.

2. The solid form dosage of claim 1, wherein therapeutic drug, biologic, hormone, peptide, or another pharmaceutical agent is delivered directly to the gastrointestinal tract.

3. The solid form dosage of claim 1, wherein naturally derived foodstuffs are delivered directly to the gastrointestinal tract for the stimulation of gut-derived serotonin to signal satiety and prolong circadian meal intervals.

4. The solid form dosage of claim 1, wherein the composition is filled inside of a capsule or other pharmaceutically acceptable form.

5. The solid form dosage of claim 1, wherein the composition is spray-dried and encapsulated in an alginate gel.

6. The solid form dosage of claim 1, wherein the pharmaceutically acceptable enteral form is between 1 and 22 mm.

7. The solid form dosage of claim 1, wherein the pharmaceutically acceptable enteral form is round, oval, oblong, square, rectangular, diamond, triangular, pentagonal or a core rod.

8. The solid form dosage of claim 1, wherein a lubricant such as magnesium stearate is added to the composition.

9. The solid form dosage of claim 1, wherein the lyophilized egg powder is between 30 and 75% by weight.

10. The solid form dosage of claim 1, wherein functional delivery is optimized to the small intestines and mimics natural homeostasis and biological production.

11. The solid form dosage of claim 1 is applied as a supplement in other species.

\* \* \* \* \*